US012676233B2

(12) United States Patent
Gamble et al.

(10) Patent No.: US 12,676,233 B2
(45) Date of Patent: Jul. 7, 2026

(54) CONFIGURABLE WORKFLOWS FOR MEDICAL DEVICES

(71) Applicant: Welch Allyn, Inc., Skaneateles Falls, NY (US)

(72) Inventors: David D. Gamble, East Syracuse, NY (US); Edward T. Imboden, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 212 days.

(21) Appl. No.: 18/469,146

(22) Filed: Sep. 18, 2023

(65) Prior Publication Data

US 2024/0112801 A1 Apr. 4, 2024

Related U.S. Application Data

(60) Provisional application No. 63/377,569, filed on Sep. 29, 2022.

(51) Int. Cl.
*G16H 40/67* (2018.01)
*G16H 70/20* (2018.01)

(52) U.S. Cl.
CPC ............. *G16H 40/67* (2018.01); *G16H 70/20* (2018.01)

(58) Field of Classification Search
None
See application file for complete search history.

(56) References Cited

U.S. PATENT DOCUMENTS

| | | | |
|---|---|---|---|
| 9,526,920 B2 | 12/2016 | Tanis et al. | |
| 10,285,589 B2 | 5/2019 | Hart et al. | |
| 10,772,495 B2 | 9/2020 | Farchione et al. | |
| 10,984,128 B1* | 4/2021 | Hoffer | G16B 50/30 |
| 10,993,613 B2 | 5/2021 | Hart et al. | |
| 11,138,732 B2 | 10/2021 | Hart et al. | |
| 11,594,319 B2* | 2/2023 | Yousfi | G16H 80/00 |
| 2006/0074463 A1 | 4/2006 | Seeberger et al. | |
| 2009/0063187 A1* | 3/2009 | Johnson | H04L 45/308 |
| | | | 705/2 |
| 2009/0063193 A1* | 3/2009 | Barton | G08B 21/02 |
| | | | 340/539.11 |
| 2013/0245387 A1 | 9/2013 | Patel | |
| 2014/0073880 A1 | 3/2014 | Boucher et al. | |
| 2017/0177801 A1* | 6/2017 | Ryan | G16H 50/30 |
| 2017/0228501 A1* | 8/2017 | Turner, Jr. | G06Q 30/0205 |
| 2019/0108909 A1* | 4/2019 | Lee | G01C 21/206 |
| 2019/0209022 A1* | 7/2019 | Sobol | A61B 5/02055 |

(Continued)

OTHER PUBLICATIONS

International Search Report and Written Opinion for Application No. PCT/US2023/033025 mailed Jan. 24, 2024.

*Primary Examiner* — David J Stoltenberg
(74) *Attorney, Agent, or Firm* — Merchant & Gould P.C.

(57) ABSTRACT

A system for modifying a workflow on a medical device receives a request for activating a service type on the medical device. The system determines a geographic location of the medical device, and determines whether the service type is authorized for use in the geographical location of the medical device. The system activates the service type on the medical device when the service type is available for activation on the medical device and the service type is authorized for the geographic location of the medical device. The system modifies the workflow on the medical device based on the service type.

20 Claims, 8 Drawing Sheets

(56)  References Cited

U.S. PATENT DOCUMENTS

| | | | |
|---|---|---|---|
| 2019/0228863 A1* | 7/2019 | Dharwad | G16H 20/17 |
| 2019/0357769 A1* | 11/2019 | Wang | A61B 3/12 |
| 2020/0405148 A1 | 12/2020 | Tran | |
| 2021/0287794 A1* | 9/2021 | Alden | G16H 20/17 |
| 2022/0039653 A1 | 2/2022 | Meyerson et al. | |
| 2022/0084664 A1* | 3/2022 | Ginsburg | G16H 15/00 |
| 2022/0139568 A1* | 5/2022 | Roh | G16H 50/20 |
| | | | 340/539.12 |
| 2023/0016417 A1 | 1/2023 | Hart | |
| 2023/0102555 A1* | 3/2023 | Pandya | G16H 40/67 |
| | | | 705/3 |
| 2024/0005432 A1* | 1/2024 | Aman | G06Q 30/0601 |

* cited by examiner

600

602
Receive Request

604
Determine Location

606
Assign Service Type

608
Modify Workflow

CONFIGURABLE WORKFLOWS FOR MEDICAL DEVICES

BACKGROUND

Diabetic retinopathy and other eye diseases can be diagnosed by studying an image of the retina. Retinal images can be reviewed manually by a clinician. However, manual review is labor-intensive process and subject to human error. In some instances, an overread service is used to provide additional resources for analyzing retinal images.

SUMMARY

In general terms, the present disclosure relates to configurable workflows for medical devices. Various aspects are described in this disclosure, which include, but are not limited to, the following aspects.

One aspect relates to a system for modifying a workflow on a medical device, the system comprising: at least one processing device; and a memory device storing instructions which, when executed by the at least one processing device, cause the at least one processing device to: receive a request for activating a service type on the medical device; determine a geographic location of the medical device; determine whether the service type is authorized for use in the geographical location of the medical device; activate the service type on the medical device when the service type is available for activation on the medical device and the service type is authorized for the geographic location of the medical device; and modify the workflow on the medical device based on the service type.

Another aspect relates to a method for modifying a workflow on a medical device, the method comprising: receiving a request for activating a service type on the medical device; accessing a network database having a service type sub-database listing service types available for activation on the medical device and a regulations sub-database storing regulatory clearance data based on geographic region for the service types available for activation; determining whether the service type in the request is available for activation on the medical device by checking the service type sub-database; determining a geographic location of the medical device; determining whether the service type in the request is authorized for the geographic location of the medical device by checking the regulations sub-database; and activating the service type on the medical device when the service type is available for activation on the medical device and the service type is authorized for the geographic location of the medical device; and modifying the workflow on the medical device based on the service type.

Another aspect relates to a non-transitory computer-readable data storage medium comprising instructions that, when executed, cause at least one computing device to: receive a request for activating a service type on a medical device; access a network database having a service type sub-database listing service types available for activation on the medical device and a regulations sub-database storing regulatory clearance data based on geographic region for the service types available for activation; determine whether the service type is available for activation on the medical device by checking the service type sub-database; determine a geographic location of the medical device; determine whether the service type is authorized for the geographic location of the medical device by checking the regulations sub-database; and activate the service type on the medical device when the service type is available for activation on the medical device and the service type is authorized for the geographic location of the medical device; and modify a workflow on the medical device based on the service type.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
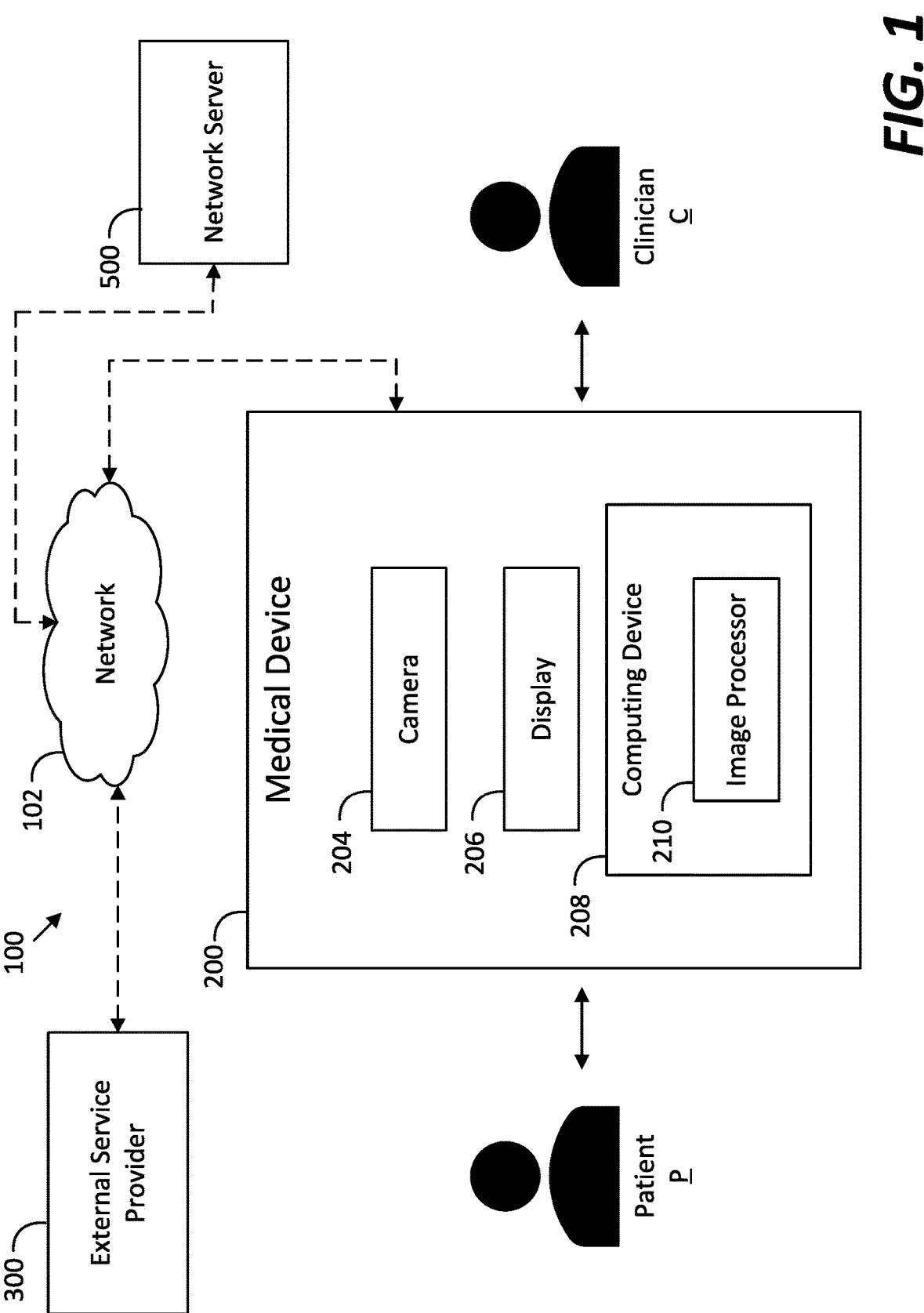
FIG. 1 schematically illustrates an example of a system for capturing and analyzing diagnostic data, the system including a medical device connected to a network server.

FIG. 1 schematically illustrates an example of a system 100 for capturing and analyzing diagnostic data. The system 100 includes a medical device 200 connected to a network 102. The medical device 200 is operable by a clinician C to capture the diagnostic data from a patient P, and to transmit the diagnostic data to an external service provider 300. The external service provider 300 returns an analysis and/or a clinical report based on the captured diagnostic data to the medical device 200. In some examples, the external service provider 300 provides overread services for the diagnostic data captured by the medical device 200.

In the example illustrated in FIG. 1, the medical device 200 is an eye imager that captures one or more fundus images of the patient P's eyes to screen, monitor, and/or diagnose one or more eye diseases such as diabetic retinopathy, macular degeneration, glaucoma, and papilledema. As used herein, "fundus" refers to the eye fundus and includes the retina, optic disc, macula, fovea, retinal blood vessels, and other anatomical structures of the eye.

The clinician C can use the medical device 200 to transmit the fundus images to the external service provider 300 via the network 102, and to receive an analysis and/or a diagnostic report based on the fundus images from the external service provider 300 via the network 102. In examples where the external service provider 300 provides overread services, the clinician C who operates the medical device 200 is different from the clinician C who evaluates the fundus images captured by the medical device 200. In some examples, the external service provider 300 uses artificial intelligence, machine learning, and similar techniques to analyze the fundus images captured by the medical device 200 for disease screening, monitoring, and/or diagnosis.

In alternative examples, the system 100 can include various types of medical and/or diagnostic devices connected to the external service provider 300 via the network 102 such as including, without limitation, otoscopes, ophthalmoscopes, dermatoscopes, and electrocardiogram (EKG) machines. Thus, the disclosure provided herein is not necessarily limited to fundus imagers and may apply to other types of medical and/or diagnostic devices.

The medical device 200 further includes a computing device 208 in communication with a camera 204 and a display 206. In this example, the computing device 208 includes an image processor 210 coupled to the camera 204 and in communication with the display 206.

The medical device 200 is operated by the clinician C to create a set of digital images of the patient P's eye fundus. As an example, the fundus images created by the medical device 200 can be used to screen for an eye disease such as diabetic retinopathy. As a further example, the fundus images created by the medical device 200 can be used to diagnose a disease such as diabetic retinopathy or monitor the progression of a disease such as diabetic retinopathy.

One technique for fundus imaging requires mydriasis, or the dilation of the patient P's pupil, which can be painful and/or inconvenient to the patient P. The medical device 200 does not require a mydriatic drug to be administered to the patient P before imaging. However, the medical device 200 can image the fundus when a mydriatic drug has been administered.

The camera 204 is communicatively connected to the image processor 210. In this example, the camera 204 is a digital camera that can include a lens, an aperture, and a sensor array. In some examples, the camera 204 lens is a variable focus lens, such as a lens moved by a step motor, or a fluid lens, also known as a liquid lens in the art. The camera 204 is configured to record images of the fundus one eye at a time. In other examples, the camera 104 is configured to record an image of both eyes substantially simultaneously. In such examples, the medical device 200 can include two separate cameras, each capturing a fundus image of an eye of the patient P.

The display 206 is communicatively coupled to the image processor 210. The display 206 functions to reproduce the images created by the camera 204 in a size and format readable by the clinician C. For example, the display 206 can include a liquid crystal display (LCD) and/or active matrix organic light emitting diode (AMOLED) display. In some examples, the display 206 includes a touchscreen that operates as an input device for medical device 200.

The network 102 may include any type of wireless network, wired network, or any combination of wireless and wired networks. Wireless connections can include broadband cellular network connections (e.g., 4G and 5G) and connections made using protocols such as 802.11a, b, and/or g. In some examples, wireless connections can be accomplished using one or more wireless protocols, such as Bluetooth, Wi-Fi, radio-frequency identification (RFID), Zigbee. In some examples, wired connections can be accomplished through Ethernet. In some examples, the network 102 includes the Internet. Other configurations are possible.

In FIG. 1, a network server 500 is communicatively connected to the medical device 200 via the network 102. As will be described in more detail, the network server 500 operates to activate one or more workflows and/or features on the medical device 200.

Figure 2:
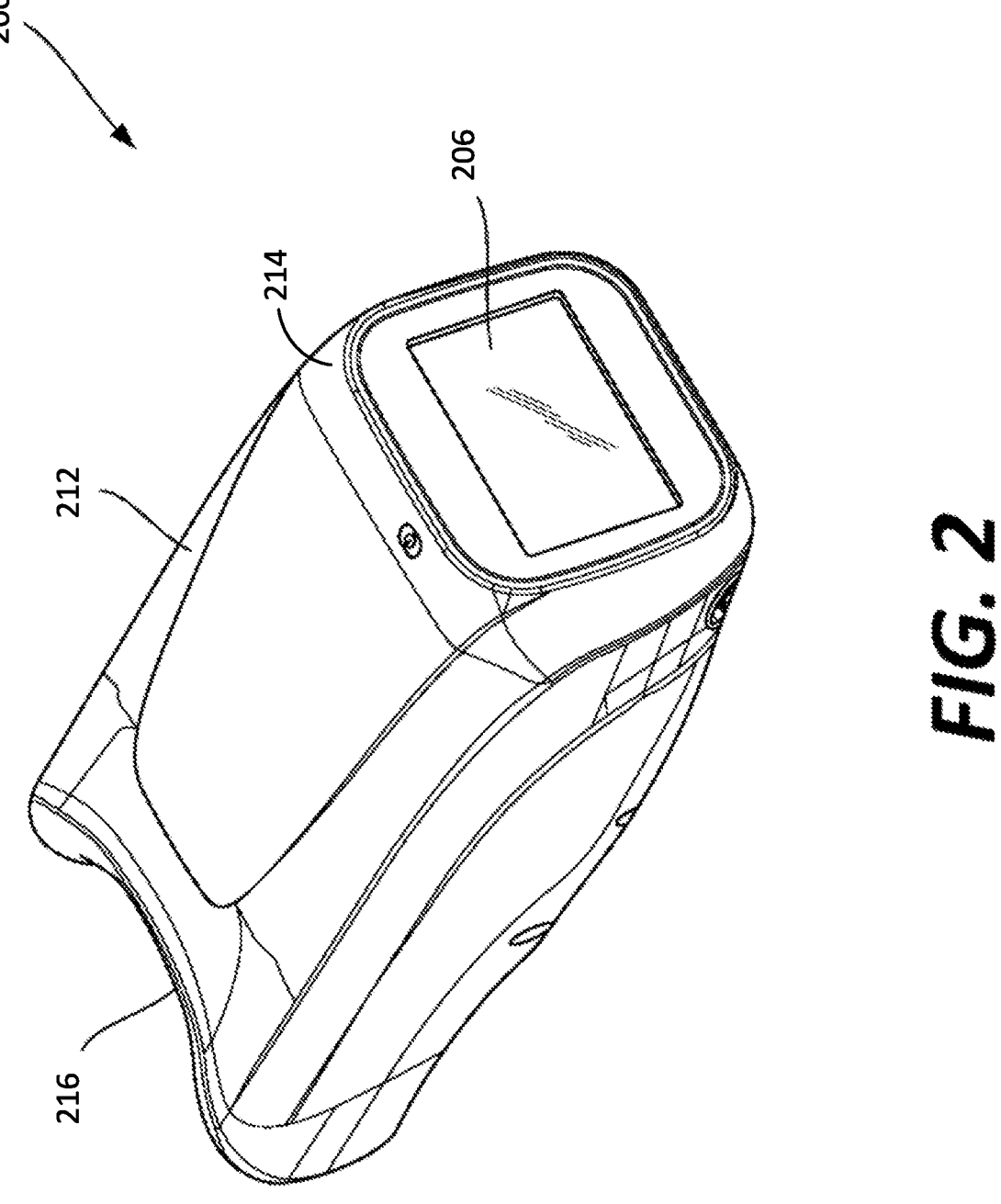
FIG. 2 illustrates an isometric view of an example of the medical device in the system of FIG. 1, the medical device being shown from a clinician perspective.
Figure 3:
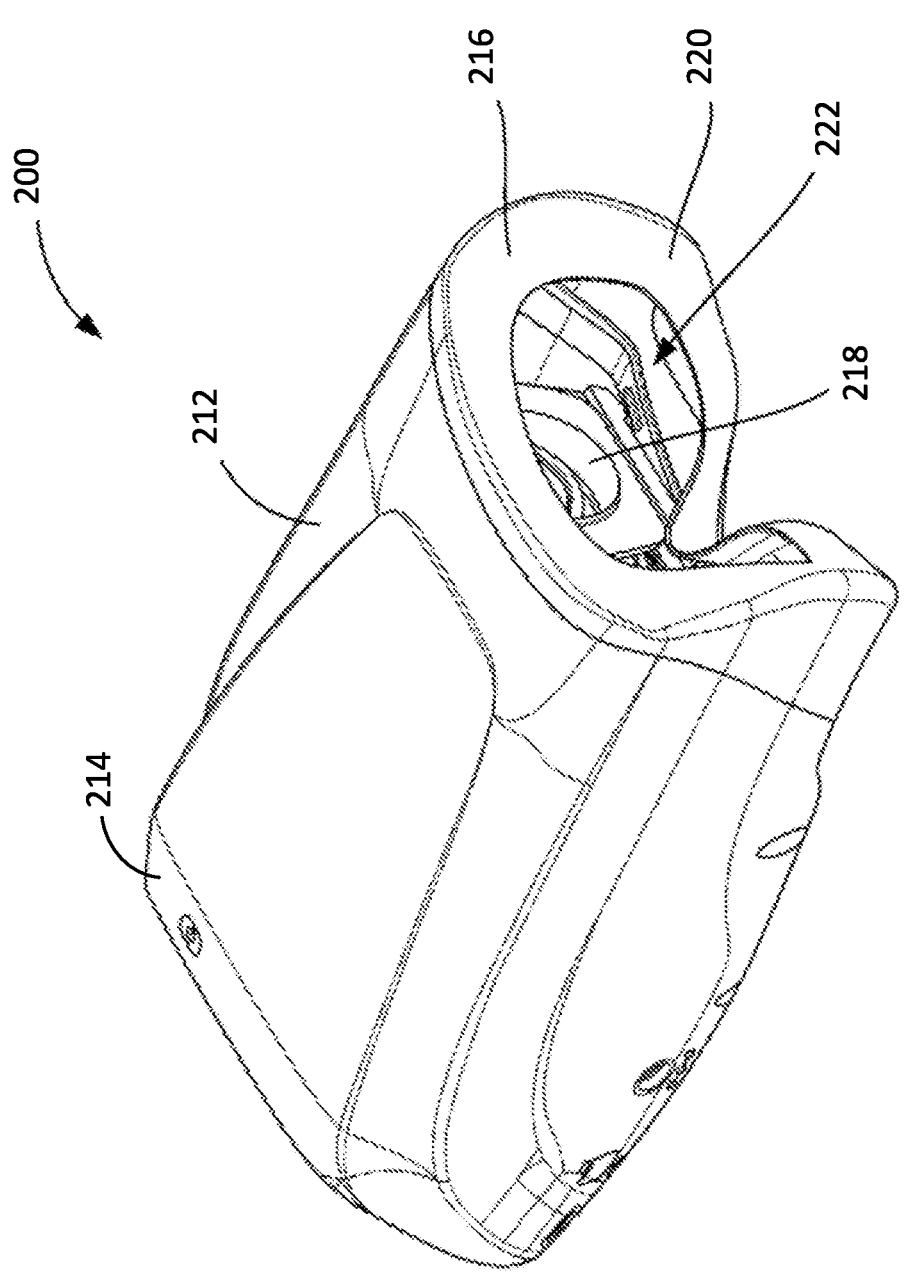
FIG. 3 illustrates another isometric view of the medical device of FIG. 2, the medical device being shown from a patient perspective.
Figure 4:
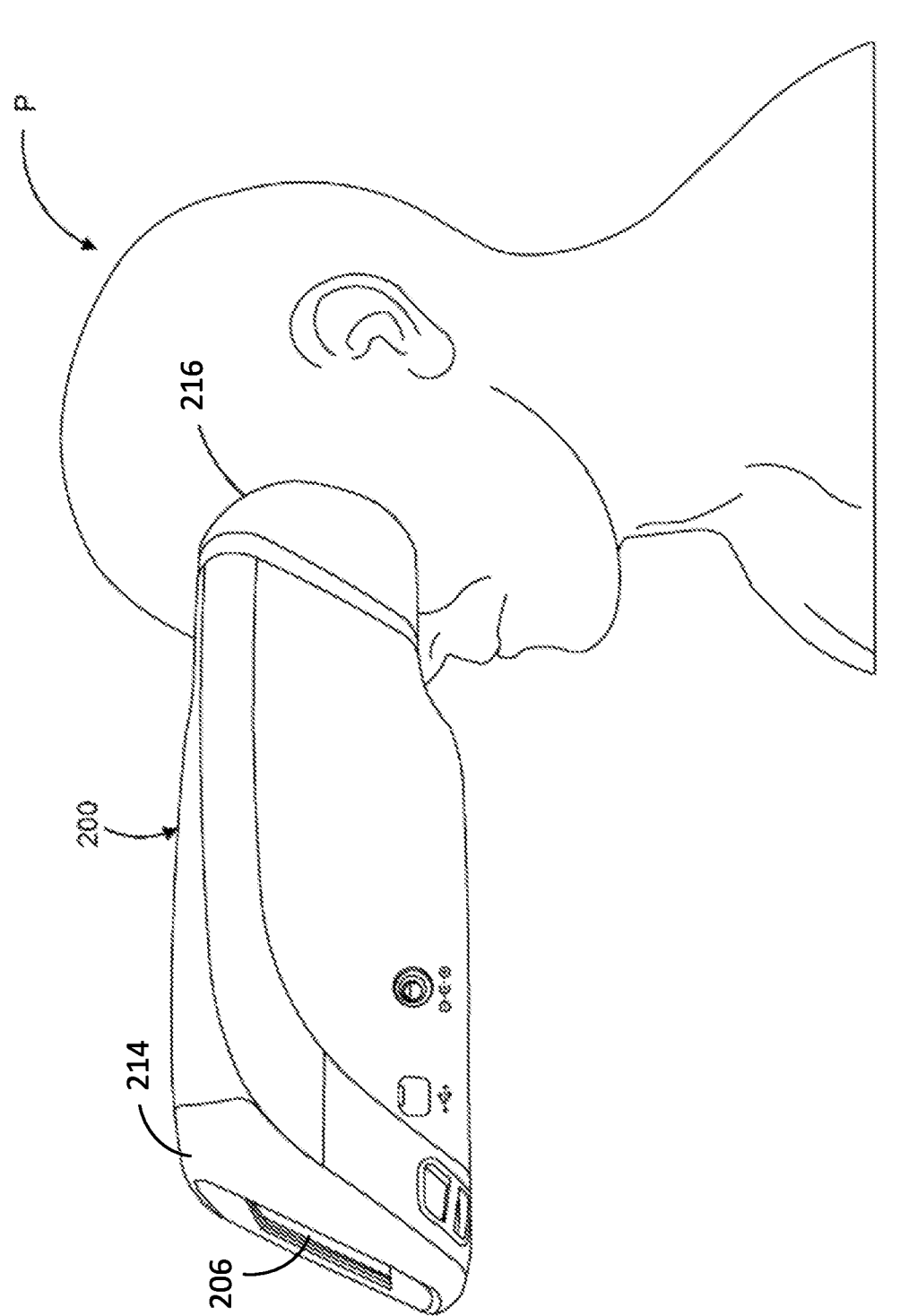
FIG. 4 illustrates the medical device of FIG. 2 positioned on a patient's head to capture diagnostic data from the patient.

FIG. 2 illustrates an isometric view of an example of the medical device 200 from a perspective of the clinician C. FIG. 3 illustrates an isometric view of the medical device 200 from a perspective of the patient P. FIG. 4 illustrates the medical device 200 while being used to capture diagnostic data from a patient. Referring now to FIGS. 1-4, the medical device 200 includes a housing 212 sized and shaped for handheld use. The housing 212 extends from a first end 214 facing the clinician C to a second end 216 that faces the patient P during use.

As shown in FIG. 2, the housing 212 supports the display 206 at the first end 214. In examples where the display 206 includes a touchscreen, the display 206 can display controls for operating the camera 204 to capture fundus images. Once the fundus images have been captured by the camera 204, and the display 206 can display the fundus images for viewing by the clinician C. The housing 212 can additionally support one or more user input buttons at the first end 214. The medical device 200 enables the clinician C to implement one or more automatic and/or manual workflows for the capture of fundus images of the patient P's eyes.

In alternative examples, the display 206 is provided on a device separate from the medical device 200. For example, the display 206 can be provided on a smartphone, a tablet computer, or other external monitor that can communicate with the medical device 200 such as through the network 102, and/or through an additional network.

As shown in FIGS. 3 and 4, the housing 212 at the second end 216 is sized and shaped to engage one or both eyes of the patient P. The second end 216 of the housing 212 includes a surface 220 for engaging the patient P's head. For example, the surface 220 is configured to be positioned against the patient P's face and to surround both eyes of the patient P. The camera 204 is positioned within a cavity 222 formed inside the housing 212.

As further shown in FIG. 3, the housing 212 at the second end 216 includes one or two apertures 218 for imaging one or both eyes of the patient at a time. In some examples, a positional guide such as an adjustable chin rest can be used to help align the patient's P eyes with the one or two apertures 218. In some examples, the housing 212 supports means for raising and lowering the camera 204 for alignment with the patient P's eyes. In some examples, the camera 204 can move in three directions to image the fundus of both eyes of the patient P while the housing 212 is held positioned against the patient P's head, as shown in FIG. 4.

As shown in FIG. 4, once the patient P's eyes are aligned, the clinician C can initiate an image capture sequence on the medical device 200. In examples where the display 206 includes a touchscreen, the clinician C can select the image capture sequence on the display 206 positioned at the first end 214 of the housing 212 that faces the clinician C.

Figure 5:
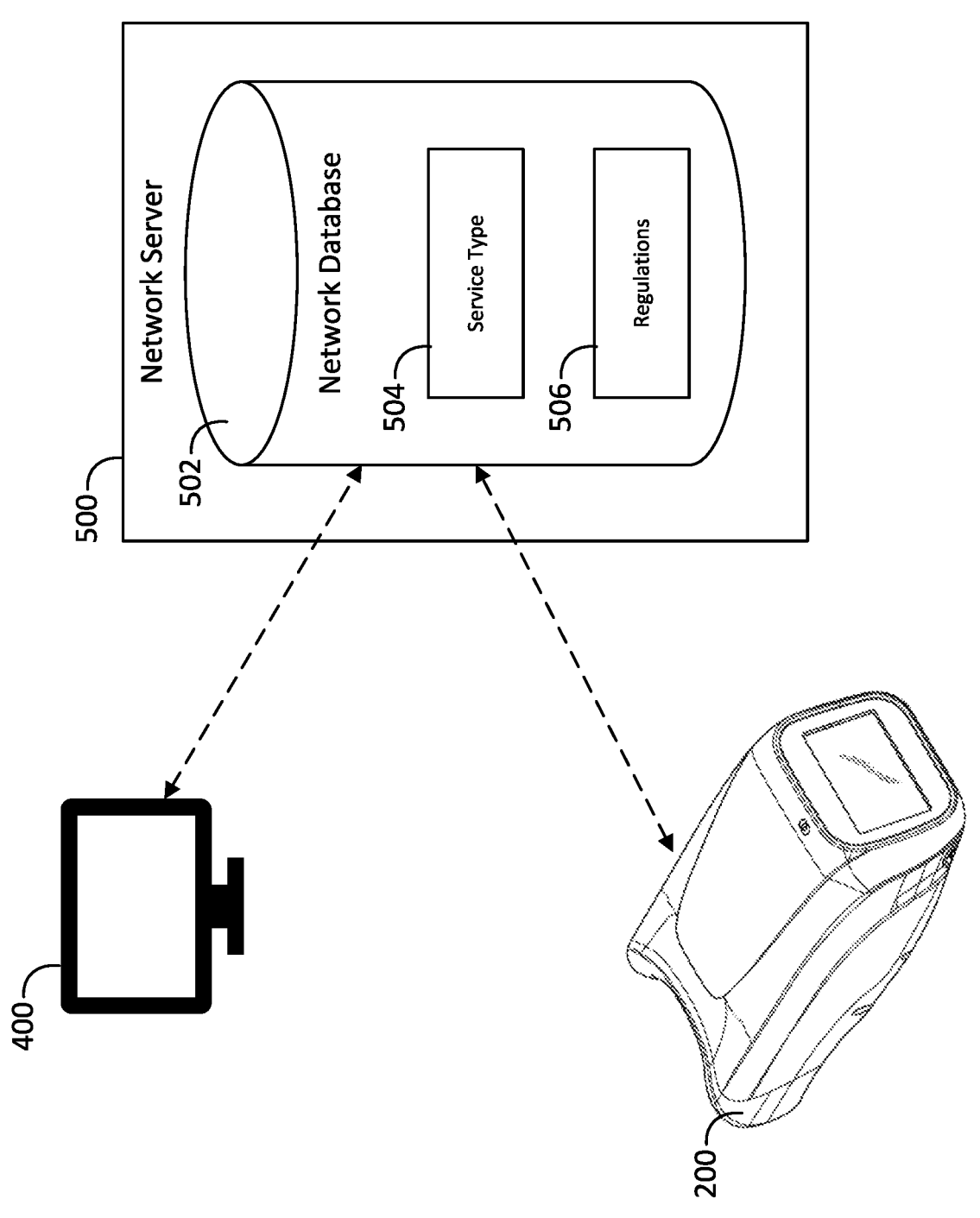
FIG. 5 schematically illustrates an example of communications between the medical device and network server of FIG. 1, and an accessory device.

FIG. 5 schematically illustrates an example of communications between the medical device 200, the network server 500, and an accessory device 400. These communications can be performed over the network 102 in accordance with the examples described above.

The network server 500 includes the network database 502 that stores data pertaining to the availability of workflows and features for activation on the medical device 200. In this example, the network database 502 stores two levels of authorization for activating and deactivating the workflows and features on the medical device 200.

A first level includes a service type sub-database 504 that lists all service types that are available for activation on the medical device 200. As used herein, a service type includes workflows and features that can be performed on the medical device 200.

As an illustrative example, a first service type can define a workflow for the medical device 200 to capture one or more fundus images, and to send the one or more fundus images to the external service provider 300 for an overread service to provide an analysis by a board certified ophthalmologist. As another example, a second service type can define a workflow for the medical device 200 to capture one or more fundus images without sending the one or more fundus images to the external service provider 300 (i.e., without an overread service).

A third service type can define a workflow for the medical device 200 to capture one or more fundus images, and to send the one or more fundus images to the external service provider 300 for an automated analysis by an artificial intelligence algorithm and/or a machine learning algorithm performed by the external service provider 300. As another example, a fourth service type can define a workflow for the medical device 200 to capture one or more fundus images, and to execute an artificial intelligence algorithm and/or a machine learning algorithm on the medical device 200 for an automated analysis of the one or more fundus images without sending the one or more fundus images to the external service provider 300. As a further example, a fifth service type can define a workflow for the medical device 200 to capture one or more fundus images, and to send the one or more fundus images to the external service provider 300 for an overread service to provide an analysis by a board certified ophthalmologist and for an automated analysis by an artificial intelligence algorithm and/or a machine learning algorithm. In such examples, the artificial intelligence algorithm and/or the machine learning algorithm (whether performed by the external service provider 300 or the medical device 200) can include screening for one or more disease states such as diabetic retinopathy, macular degeneration, glaucoma, papilledema, and other eye diseases. Additional examples of service types defining workflows for execution on the medical device 200 are possible.

Further examples of the workflows that can be executed on the medical device 200 based on a service type assigned and/or activated on the medical device 200 can include guiding a user to operate the medical device 200 to capture an image showing a region of interest, to align an optical axis of the medical device 200 with the region of interest, to guide the user through an eye fundus image capturing process, to execute an automated script for capture of the eye fundus image, to allow for manual capture of the eye fundus image, to automatically move a camera until a bright spot associated with a reflection of a cornea of the eye is positioned for automatic capture of the image of the eye, to automate a quality assessment of a digital eye fundus image, to estimate one or more disease states, to provide a workflow based on a risk score for a given patient, to perform a microvascular assessment based on captured eye images, to calculate one or more vital signs based on an eye fundus video, and the like.

In some examples, the service types available for activation on the medical device 200 are based on a subscription to the network server 500 of the clinician C or customer of the medical device 200. In some examples, the service types available for activation on the medical device 200 are updated based on requests by the clinician C or customer of the medical device 200, and/or changes in the subscription to the network server 500. The accessory device 400 is operated by authorized personnel such as a technician of the manufacturer of the medical device 200 to assign, update, or change the service types available for activation on the medical device.

As an illustrative example, the service type sub-database 504 can include a table where service types are initially assigned, and thereafter new service types are added using the accessory device 400 such as by adding new rows in the table. In some examples, the service types are added consecutively to the table of the service type sub-database 504 rather than edited, which allows for a history of the service types to be viewed and queried.

In some examples, the authorized technician can use the accessory device 400 to adjust values in a column titled "Active" of the table which sets the active state for each service type assigned to the medical device 200. To change the state of a service type assigned to the medical device 200, the authorized technician can access the service type sub-database 504 and set the Active column to 1 to activate the service type, or set the Active column to 0 to deactivate the service type. As described above, the service types assigned to the medical device 200 can be updated based on requests by the clinician C or customer of the medical device 200, or based on changes in the subscription of the medical device 200 to the network server 500.

As further shown in FIG. 5, a second level for activating and deactivating the workflows and features on the medical device 200 includes a regulations sub-database 506 that stores regulatory clearance data on the service types that are available for activation on the medical device 200. The regulatory clearance data is based on the geographic region where the medical device 200, the clinician C, and/or the customer of the medical device 200 are located. As an illustrative example, a service type available for activation on the medical device 200 includes machine learning algorithms performed by the external service provider 300 on the fundus images captured by the medical device 200, and in some instances, the machine learning algorithms are approved by a regulatory body in one geographic region (e.g., the Food and Drug Administration (FDA) of the United States), while the same algorithms are not approved by another regulatory body in another geographic region (e.g., the European Medicines Agency (EMA) of the European Union). Additional examples are contemplated.

The regulations sub-database 506 can include a table that lists all valid service types available within a particular geographic region. When a particular service type is made available for a particular geographic region (i.e., when authorized for use by a governing body such as the FDA, EMA, etc.), the service type is added by the accessory device 400 as a row in the table of the regulations sub-database 506 for associating the service type to the geographic region.

In this example, when a row is included in the table of the regulations sub-database 506 such that a service type is authorized for use in the geographic region where the medical device 200, the clinician C, and/or the customer of the medical device 200 are located, and the service type is set to active in the table of the service type sub-database 504, the service type is made available for the medical device. Otherwise, when a row is missing in the table of the regulations sub-database 506 such that the service type is not authorized for use in the geographic region where the medical device 200, the clinician C, and/or the customer of the medical device 200 are located, or the service type is set to deactivate in the table of the service type sub-database 504, the service type is not available for the medical device.

Figure 6:
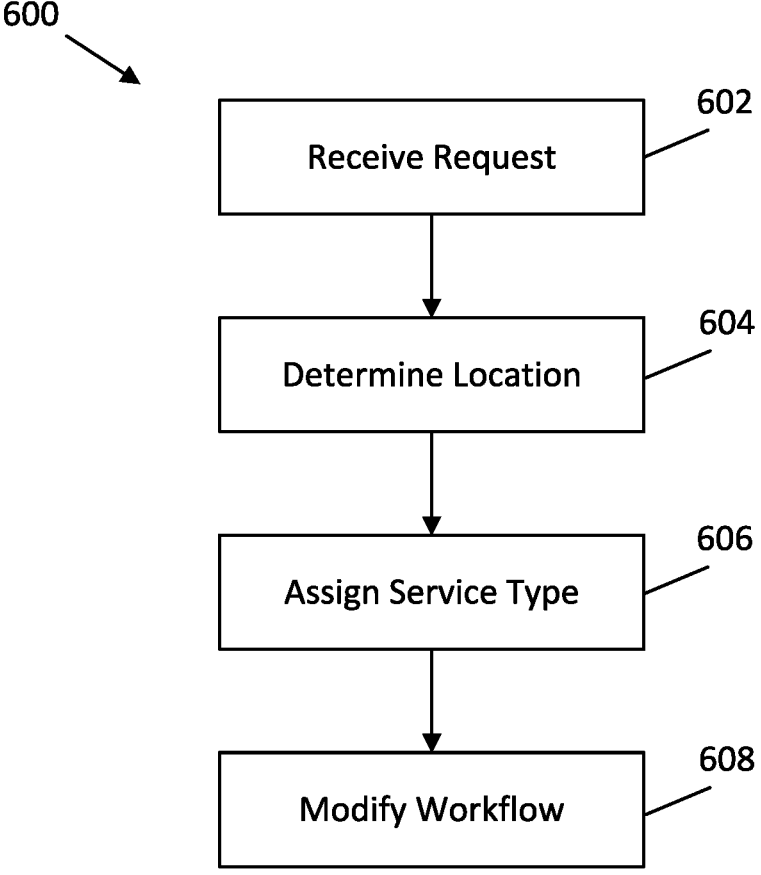
FIG. 6 schematically illustrates an example of a method of performing a workflow on the medical device of FIG. 1.

FIG. 6 schematically illustrates an example of a method 600 of performing a workflow on the medical device 200. As shown in FIG. 6, the method 600 includes an operation 602 of receiving a request for a service type to be activated on the medical device 200. In some examples, the request for the service type is received when a customer of the medical device 200 registers and/or sets up the medical device 200 for the first time after purchase. In some examples, the request for the service type is received after the medical device 200 has been used such as when the customer of the medical device 200 requests a new service type to be activated.

The method 600 includes an operation 604 of determining a location of the medical device 200, the clinician C, and/or the customer of the medical device 200. In some examples, the location of the customer of the medical device 200 is known from the purchase order of the medical device 200 received from the customer.

In some examples, operation 604 can include using the connection established between the medical device 200 and the network 102 to determine the geographical location of the medical device 200. For example, when the network 102 includes the Internet, operation 604 can including using an Internet Protocol address (IP address) of the medical device 200 to determine the geographical location of the medical device 200. As another example, when the network 102 includes broadband cellular network connections, operation 608 can including using the cellular network connection of the medical device 200 to determine the geographical location of the medical device 200. In further examples, the medical device 200 can include a dedicated device for determining its location such as a Global Positioning System (GPS) tracker. Additional examples for determining the location of the medical device 200 are possible.

Next, the method 600 includes an operation 606 of assigning the service type to the medical device based on the request for the service type received in operation 602, and the location of the medical device 200, the clinician C, and/or the customer of the medical device 200 determined in operation 604. Operation 606 can include accessing the network database 502 that includes the service type sub-database 504 listing all service types available for activation on the medical device 200, and the regulations sub-database 506 storing regulatory clearance information of the geographic region where the medical device 200, the clinician C, and/or the customer of the medical device 200 are located. Operation 606 can include determining whether the requested service type is activated or deactivated in the service type sub-database 504. Operation 606 can further include determining whether the requested service type is listed as authorized for the geographic location of the medical device 200, the clinician C, and/or the customer of the medical device 200 in regulations sub-database 506.

When the requested service type is available for activation on the medical device 200 and is authorized for the geographic location of the medical device 200, the clinician C, and/or the customer of the medical device 200, operation 608 activates the requested service type on the medical device 200. Otherwise, when the requested service type is not available for activation on the medical device 200 or is not authorized for the geographic location of the medical device 200, the clinician C, and/or the customer of the medical device 200, operation 608 blocks access to the requested service type on the medical device 200.

After the requested service type is activated on the medical device 200, the method 600 can further include an operation 608 of modifying a workflow performed on the medical device 200 based on the activation of the requested service type. For example, the workflow can be modified to capture diagnostic data (e.g., fundus images captured by the camera 204), and to send the diagnostic data to the external service provider 300 for an overread service to provide an analysis by a medical specialist such as a board certified ophthalmologist. As another example, the workflow can be modified to capture diagnostic data (e.g., fundus images captured by the camera 204) without sending the diagnostic data to the external service provider 300. As a further example, the workflow can be modified to capture diagnostic data (e.g., fundus images captured by the camera 204), and to send the diagnostic data to the external service provider 300 for an automated analysis by an artificial intelligence algorithm and/or a machine learning algorithm performed by the external service provider 300. As another illustrative example, the workflow can be modified to capture diagnostic data (e.g., fundus images captured by the camera 204), and to execute an artificial intelligence algorithm and/or a machine learning algorithm locally on the medical device 200 for an automated analysis of the diagnostic data. As a further example, the workflow can be modified to capture diagnostic data (e.g., fundus images captured by the camera 204), and to send the diagnostic data to the external service provider 300 for an overread service to provide an analysis by a medical specialist and for an automated analysis by an artificial intelligence algorithm and/or a machine learning algorithm. In such examples, the artificial intelligence algorithm and/or the machine learning algorithm (whether performed by the external service provider 300 or the medical device 200) can include screening for one or more disease states such as diabetic retinopathy, macular degeneration, glaucoma, papilledema, and other diseases. Additional examples of service types that define and/or modify workflows for execution on the medical device 200 are possible.

Figure 7:
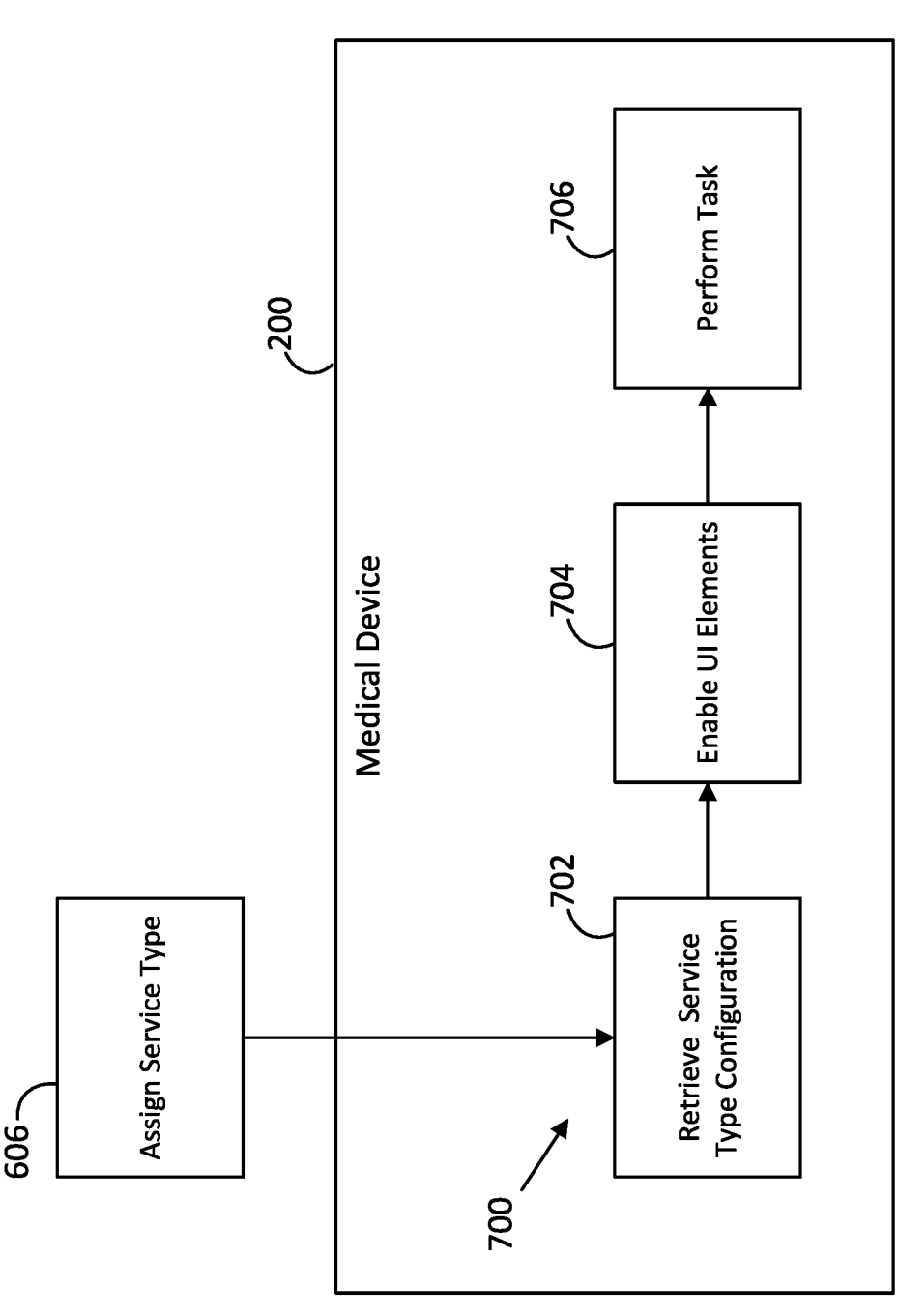
FIG. 7 schematically illustrates an example of a method of modifying a workflow on the medical device of FIG. 1 based on a service type assigned to the medical device.

FIG. 7 schematically illustrates an example of a method 700 of modifying a workflow on the medical device 200 based on a service type assigned to the medical device 200. Referring now to FIG. 7, the method 700 is performed on the medical device 200. In the example illustrated in FIG. 7, the method 700 is performed after the service type has been assigned to the medical device 200, such as following operation 606 of the method 600 described above.

As shown in FIG. 7, the method 700 includes a step 702 of retrieving a configuration of the service type. In some examples, the configuration of the service type is retrieved from an account of the customer of the medical device 200. In some examples, the configuration of the service type is retrieved from the network server 500 over the network 102.

Next, the method 700 includes a step 704 of enabling user interface elements for selection on the display 206 of the medical device 200 based on the configuration of the service type retrieved in step 702. For example, one or more menu options are enabled for selection based on the configuration of the service type. As an illustrative example, a machine learning algorithm for providing an automated analysis of diagnostic data captured by the medical device 200 can be enabled for selection based on the configuration of the service type.

Next, the method 700 includes a step 706 of performing a task based on a selection of the user interface elements enabled on the display 206 of the medical device 200 in step 704. As an illustrative example, step 706 can include sending diagnostic data captured by the medical device 200 for an automated analysis by a machine learning algorithm performed on the external service provider 300. As another illustrative example, step 706 can include executing an algorithm locally on the medical device 200 for an automated analysis of the diagnostic data captured by the medical device 200. In both of these illustrative examples, the diagnostic data can include fundus images captured by the camera 204 of the medical device 200, however, the diagnostic data is not limited to fundus images and may include additional types of data.

Figure 8:
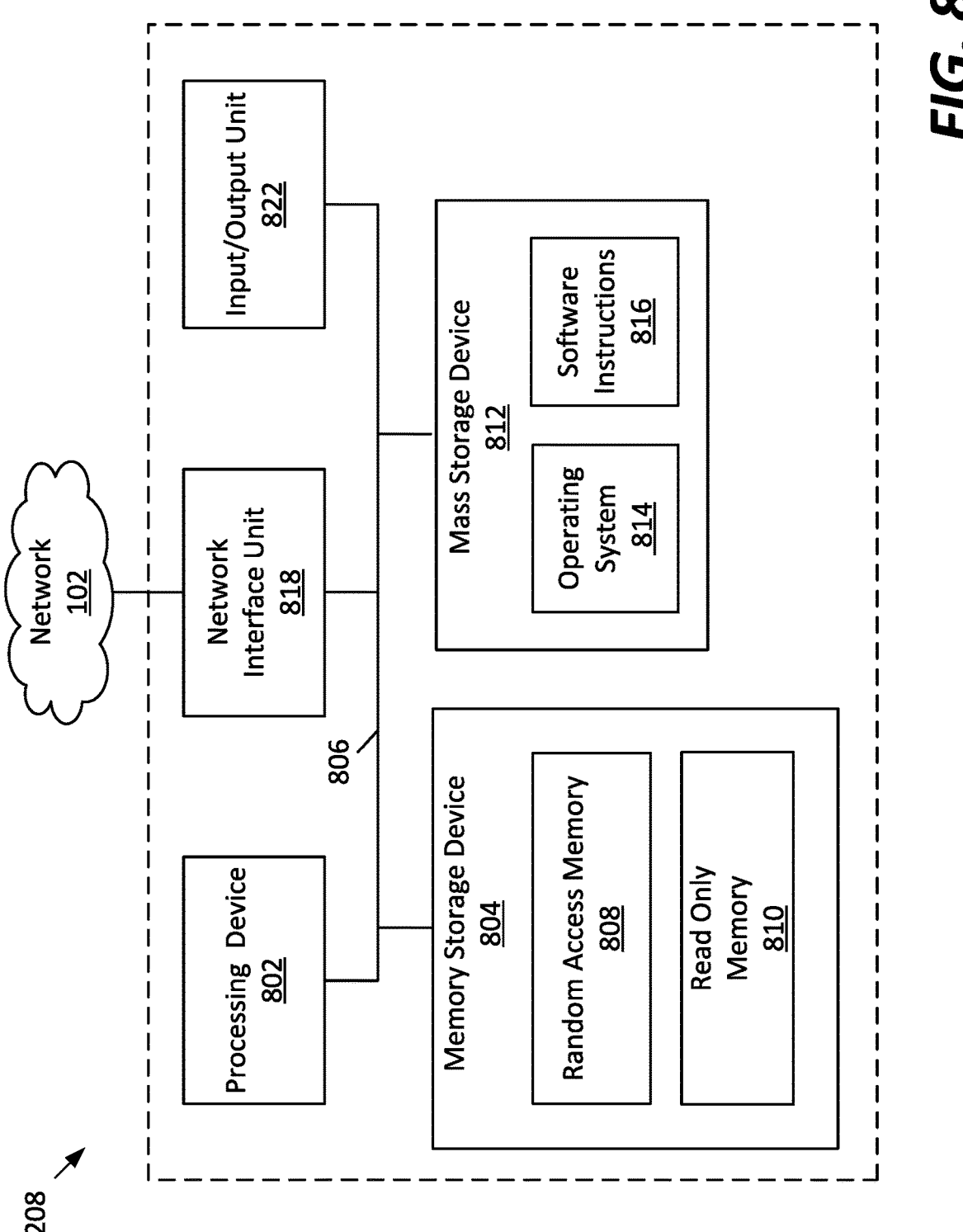
FIG. 8 schematically illustrates an example of a computing device that can be used to implement aspects of the system of FIG. 1.

FIG. 8 schematically illustrates an example of the computing device 208 that can be used to implement aspects of the system 100 such as the medical device 200, the external service provider 300, and/or the network server 500. As shown in FIG. 8, the computing device 208 includes one or more processing devices 802, a memory storage device 804, and a system bus 806 that couples the memory storage device 804 to the one or more processing devices 802. The one or more processing devices 802 can include central processing units (CPU).

As shown in FIG. 8, the memory storage device 804 can include a random-access memory ("RAM") 808 and a read-only memory ("ROM") 810. Basic input and output logic having basic routines that help to transfer information between elements within the computing device 208, such as during startup, can be stored in the ROM 810.

The computing device 208 can further include a mass storage device 812 that can include an operating system 814, and store software instructions 816. The mass storage device 812 is connected to the one or more processing devices 802 through the system bus 806. The mass storage device 812 and associated computer-readable data storage media provide non-volatile, non-transitory storage for the computing device 208.

Although the description of computer-readable data storage media contained herein refers to the mass storage device 812, it should be appreciated by those skilled in the art that computer-readable data storage media can be any available non-transitory, physical device or article of manufacture from which the one or more processing devices 802 can read data and/or instructions. The computer-readable storage media can be comprised of entirely non-transitory media. The mass storage device 812 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The computing device 208 operates in a networked environment using logical connections to the other devices through the network 102. The computing device 208 connects to the network 102 through a network interface unit 818 connected to the system bus 806. The network interface unit 818 can also connect to additional types of communications networks and devices, including Bluetooth, Wi-Fi, and cellular telecommunications networks including 4G and 5G networks. The network interface unit 818 can connect the computing device 208 to additional networks, systems, and devices. The computing device 208 further includes an input/output unit 822 for receiving and processing inputs and outputs. In examples where the display 206 is a touch-screen, the display 206 is both an input and output device.

The mass storage device 812 and the RAM 808 can store software instructions and data. The software instructions can include an operating system 814 for operating the computing device 208. The mass storage device 812 and/or the RAM 808 can also store software instructions 816, which when executed by the processing device 802, provide the various functions and aspects of the computing device 208 discussed herein.

The various embodiments described above are provided by way of illustration only and should not be construed to be limiting in any way. Various modifications can be made to the embodiments described above without departing from the true spirit and scope of the disclosure.

What is claimed is:

1. A system for modifying a workflow on a medical device, the system comprising:
   at least one processing device; and
   a memory device storing instructions which, when executed by the at least one processing device, cause the at least one processing device to:
      receive a request for activating a service type on the medical device;
      extract network connectivity data of the medical device used to establish network connections;
      determine a geographic location of the medical device using the network connectivity data;
      access a service type database that stores service types in a table structure where the service types are stored as separate rows with a state control column containing values that support multiple activation states for the service types;
      determine whether the service type is authorized for use in the geographic location of the medical device;
      activate the service type on the medical device when the service type is available for activation on the medical device and the service type is authorized for the geographic location of the medical device; and
      modify the workflow on the medical device based on the service type.

2. The system of claim 1, wherein the instructions, when executed by the at least one processing device, further cause the at least one processing device to:
   block access to the service type on the medical device when the service type is not available for activation on the medical device or the service type is not authorized for the geographic location of the medical device.

3. The system of claim 1, wherein the instructions, when executed by the at least one processing device, further cause the at least one processing device to:
   access a network database having a service type sub-database listing service types available for activation on the medical device and a regulations sub-database storing regulatory clearance data based on geographic region for the service types available for activation.

4. The system of claim 3, wherein the instructions, when executed by the at least one processing device, further cause the at least one processing device to:
   check the service type sub-database to determine whether the service type in the request is available for activation on the medical device.

5. The system of claim 4, wherein the instructions, when executed by the at least one processing device, further cause the at least one processing device to:
   check the regulations sub-database to determine whether the service type in the request is authorized for the geographic location of the medical device.

6. The system of claim 3, wherein the instructions, when executed by the at least one processing device, further cause the at least one processing device to:

check the regulations sub-database to determine whether the service type in the request is authorized for the geographic location of the medical device.

7. The system of claim 1, wherein the service type includes a machine learning algorithm for providing an automated analysis of diagnostic data captured by the medical device.

8. The system of claim 7, wherein the diagnostic data includes eye fundus images.

9. The system of claim 8, wherein the automated analysis includes screening for one or more disease states.

10. A method for modifying a workflow on a medical device, the method comprising:

receiving a request for activating a service type on the medical device;

extracting network connectivity data of the medical device used to establish network connections;

accessing a network database having a service type sub-database listing service types available for activation on the medical device and a regulations sub-database storing regulatory clearance data based on geographic region for the service types available for activation, wherein the service type sub-database stores the service types in a table structure where the service types are stored as separate rows with a state control column containing values that support multiple activation states for the service types;

determining whether the service type in the request is available for activation on the medical device by checking the service type sub-database;

determining a geographic location of the medical device using the network connectivity data;

determining whether the service type in the request is authorized for the geographic location of the medical device by checking the regulations sub-database; and activating the service type on the medical device when the service type is available for activation on the medical device and the service type is authorized for the geographic location of the medical device; and modifying the workflow on the medical device based on the service type.

11. The method of claim 10, further comprising:

blocking access to the service type on the medical device when the service type is not available for activation on the medical device or the service type is not authorized for the geographic location of the medical device.

12. The method of claim 10, wherein the service type includes a machine learning algorithm for providing an automated analysis of diagnostic data captured by the medical device.

13. The method of claim 12, wherein the diagnostic data includes eye fundus images.

14. The method of claim 13, wherein the automated analysis includes screening for one or more disease states.

15. A non-transitory computer-readable data storage medium comprising instructions that, when executed, cause at least one computing device to:

receive a request for activating a service type on a medical device;

extract network connectivity data of the medical device used to establish network connections;

access a network database having a service type sub-database listing service types available for activation on the medical device and a regulations sub-database storing regulatory clearance data based on geographic region for the service types available for activation, wherein the service type sub-database stores the service types in a table structure where the service types are stored as separate rows with a state control column containing values that support multiple activation states for the service types;

determine whether the service type is available for activation on the medical device by checking the service type sub-database;

determine a geographic location of the medical device using the network connectivity data;

determine whether the service type is authorized for the geographic location of the medical device by checking the regulations sub-database; and activate the service type on the medical device when the service type is available for activation on the medical device and the service type is authorized for the geographic location of the medical device; and modify a workflow on the medical device based on the service type.

16. The non-transitory computer-readable data storage medium of claim 15, wherein the instructions, when executed, further cause the at least one computing device to:

block access to the service type on the medical device when the service type is not available for activation on the medical device or the service type is not authorized for the geographic location of the medical device.

17. The non-transitory computer-readable data storage medium of claim 15, wherein the requested service type includes a machine learning algorithm for providing an automated analysis of diagnostic data captured by the medical device.

18. The non-transitory computer-readable data storage medium of claim 17, wherein the diagnostic data includes eye fundus images.

19. The non-transitory computer-readable data storage medium of claim 18, wherein the automated analysis includes screening for one or more disease states.

20. The non-transitory computer-readable data storage medium of claim 15, wherein the requested service type includes an overread service.

* * * * *